US00RE45058E

(19) United States
(12) Reissued Patent
Blankenship et al.

(10) Patent Number: US RE45,058 E
(45) Date of Reissued Patent: Aug. 5, 2014

(54) TRANSFORMABLE INTRAVENOUS POLE

(75) Inventors: Peter Blankenship, Anoka, MN (US); Brent G. Norman, Poway, CA (US); Samuel A. Blankenship, Anoka, MN (US)

(73) Assignee: Streamline, Inc., Eden Prairie, MN (US)

(21) Appl. No.: 13/465,617

(22) Filed: May 7, 2012

Related U.S. Patent Documents

Reissue of:
(64) Patent No.: 7,918,422
Issued: Apr. 5, 2011
Appl. No.: 11/948,536
Filed: Nov. 30, 2007

U.S. Applications:
(63) Continuation-in-part of application No. 11/711,478, filed on Feb. 27, 2007, now Pat. No. 7,497,407.

(60) Provisional application No. 60/777,467, filed on Feb. 27, 2006.

(51) Int. Cl.

| | |
|---|---|
| ***A47K 1/04*** | (2006.01) |
| ***A47J 47/16*** | (2006.01) |
| ***A63B 55/08*** | (2006.01) |
| ***A47G 23/02*** | (2006.01) |
| ***F16M 11/38*** | (2006.01) |
| ***A45D 19/04*** | (2006.01) |
| ***F16M 11/24*** | (2006.01) |

(52) U.S. Cl.
USPC ..... 248/129; 248/132; 248/98; 248/150; 248/168; 248/170; 248/155.3; 248/165; 280/43.24; 280/43.17

(58) Field of Classification Search
USPC ..... 248/129, 132, 135, 136, 98, 150, 168, 248/170, 311.3, 125, 136.1, 145.6, 155.3, 248/165; 280/43.24, 43.17, 43.2; 5/503.1, 5/658
See application file for complete search history.

(56) References Cited

U.S. PATENT DOCUMENTS

| | | | | |
|---|---|---|---|---|
| 4,744,536 | A * | 5/1988 | Bancalari | 248/125.8 |
| 4,892,279 | A * | 1/1990 | Lafferty et al. | 248/125.8 |
| 7,624,953 | B2 * | 12/2009 | Silverman et al. | 248/125.1 |
| 2003/0106969 | A1 * | 6/2003 | Dillon et al. | 248/157 |
| 2005/0269464 | A1 * | 12/2005 | Adelman | 248/125.8 |
| 2007/0023587 | A1 * | 2/2007 | Eggleston et al. | 248/98 |
| 2007/0267550 | A1 * | 11/2007 | Blankenship et al. | 248/125.8 |
| 2008/0263769 | A1 * | 10/2008 | Newkirk et al. | 5/503.1 |
| 2008/0283692 | A1 * | 11/2008 | Leinen | 248/125.8 |

* cited by examiner

*Primary Examiner* — Terrell McKinnon
*Assistant Examiner* — Christopher Garft
(74) *Attorney, Agent, or Firm* — Ryan C. Smith; Larkin Hoffman Daly & Lindgren, Ltd.

(57) ABSTRACT

An intravenous (IV) pole system for supporting medical equipment having a base with legs, a mast engaged to the base, and a lifting mechanism including a gas spring engaged to the base and the mast. Each of the legs includes at least one wheel. The lifting mechanism is constructed to position the legs in an extended configuration and a retracted configuration. The lifting mechanism is further constructed to raise the legs and wheels relative to the base and relative to a surface. The lifting mechanism is configured to position the wheels proximate to the mast in the retracted configuration.

18 Claims, 8 Drawing Sheets

200
227
216
226
231
232
4
212
243
215
230
229
214
233
213
4
235
234
225
211
205
203
236
224
202
237
242
241
240
239
238
221
223
290
220
222
217
219
218
218a

TRANSFORMABLE INTRAVENOUS POLE

Matter enclosed in heavy brackets [ ] appears in the original patent but forms no part of this reissue specification; matter printed in italics indicates the additions made by reissue.

*This application is a reissue Application of U.S. Pat. No. 7,918,422 filed Nov. 30, 2007 entitled TRANSFORMABLE INTRAVENOUS POLE, which is a continuation in part of, and claims priority to, application Ser. No. 11/711,478, filed Feb. 27, 2007 now U.S. Pat. No. 7,497,407, which claims priority to provisional application No. 60/777,467 filed on Feb. 27, 2006.*

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

In some embodiments this invention relates to an improved IV pole, its manufacture, and methods of use. More particularly some embodiments relate to intravenous poles with transformable base widths to better facilitate the transport of patients.

2. Description of the Related Art

For many years, patients needing intravenous fluid transfusions have been able to be moved by a patient transportation apparatus such as a wheelchair, wheeled bed, stretcher, gurney, or the like while receiving such transfusions by the use of mobile IV poles. These IV poles, however, suffer from a number of drawbacks.

One unsatisfactory form of a mobile IV pole is a pole permanently attached to, and using out of, the patient transportation device such as that described in published US Patent Application 2006/0243500A1. This form imposes significant burdens on hospital staff as each time the patient is moved, pumps and fluid bags must both be transferred onto the transportation device before the patient is moved, and then again the pumps and fluid bags must be transferred off of the transportation device once the patient arrives at their destination. The repeated transferal of bags and pumps increases the risks of bags or pumps being dropped leading to wasted medicines needing replacement and wasted environmental services cleaning up spills as well as damage occurring to expensive pumps and equipment. Similarly the permanently attached pole makes the transportation device bulky causing awkward and difficult movement, storage, and maintenance. In the case of beds, permanently attached poles render the beds particularly bulky, and difficult to maneuver. Other problems relate to difficulty in linen changes. Further, beds with poles significantly increase the difficulty of patient transfer into and out of the bed. Most seriously of all, constant removal and re-attachment of IV bags and pumps increases the risks of IV leads being strained or pulled entirely from the patient's body, complicating a patient's treatment and potentially putting the individual at risk of infection or improper treatment.

Another unsatisfactory form of mobile IV pole is a free standing wheeled pole that is moved alongside the patient transfer apparatus such as that described in published US Patent Application 2006/0222341A1. This device unfortunately also imposes significant burdens on hospital staff. In this device one hand must be used to push the patient transfer apparatus and another to simultaneously move the IV pole. Because patient transfer apparatuses may be heavy, and not designed for one handed pushing, repeatedly utilizing one person to simultaneously move both the pole and the transfer apparatus causes significant strain, which often results in back and sprain injuries in medical personnel. Also, such pushing increases the risk of injury to a patient in that the pole may tip over onto the patient or that the patient transfer apparatus may strike walls or objects and aggravate an injury. The alternative of utilizing multiple medical personnel to transport a single patient is inefficient and cost prohibitive in an era of scarce nurses and other medical personnel.

For at least these reasons there is a need for an improved IV pole. The art referred to and/or described above is not intended to constitute an admission that any patent, publication or other information referred to herein is "prior art" with respect to this invention. In addition, this section should not be construed to mean that a search has been made or that no other pertinent information as defined in 37 CFR §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

BRIEF SUMMARY OF THE INVENTION

At least one embodiment of the invention is directed to an IV pole system for supporting medical equipment comprising: a base having at least one leg, a mast engaged to the base, and a lifting mechanism. The at least one leg comprises at least one wheel. The mast is engaged to the base and comprises a length, a top, and a bottom. The lifting mechanism comprises a gas spring engaged to the base and to the mast. The lifting mechanism is constructed and arranged to position at least one leg in an extended configuration and in a retracted configuration. At least a portion of the wheel is disposed lower than the bottom of the mast when the leg is in the extended configuration. The wheel is radially separated from the mast in the extended configuration. The lifting mechanism is further constructed and arranged to elevate the base and elevate at least a portion of the leg proximate to the mast in the retracted configuration and to position the wheel radially proximate to the mast in the retracted configuration.

At least one embodiment of the invention is directed to an IV pole in which the gas spring comprises two ends, a cylinder with a pin aperture, and a plunger. The plunger and the cylinder are movably engaged to each other. The gas spring is constructed and arranged to separate the two ends and to alter the length of the mast. The cylinder comprises a compressible fluid and is constructed and arranged to exert a pneumatic force on the plunger to separate the two ends. The cylinder is further constructed and arranged to exert a pneumatic force on the plunger to elevate the base and to position at least one leg into the retracted configuration.

At least one embodiment of the invention is directed to an IV pole having a leg is pivotably engaged to the mast. A brace can be pivotably engaged to the base and at least one leg. The brace's pivotal engagement is elevated relative to the leg's pivotal engagement when the leg is in the retracted configuration.

At least one embodiment of the invention is directed to an IV pole in which the gas spring cylinder is proximal to the base. The plunger can be proximal to the top. The gas spring can be positioned within a hollow portion of said mast. The IV pole can also have a gas release pin which is constructed and arranged to be inserted into and separated from a pin aperture and to actuate the gas spring. A pedal having a pedal lever can be engaged to the gas release pin. The pedal lever can be constructed and arranged to insert and separate the gas release pin relative to said pin aperture.

At least one embodiment of the invention is directed to an IV pole further comprising at least one wing extending substantially parallel to the mast and being engaged to the mast. The wing may be removably engaged to the mast. A halo may be engaged to the mast proximate to the top. The halo comprises a outer frame having at least one hook projecting away from the frame.

At least one embodiment of the invention is directed to an IV pole system further comprising a pole mount. The pole mount comprises a horizontally sliding bar engaged to both a vertically extending support bar and at least one engagement member. The vertically extending support bar comprises an elevating mechanism and one or more gripping members. The gripping members are constructed and arranged for engagement to the mast. The elevating mechanism is constructed and arranged to adjust a vertical position of the mast. The horizontally sliding bar is constructed and arranged to adjust a horizontal separation distance between the at least one engagement member and the vertically extending support bar. The at least one engagement member can be constructed and arranged to engage a hospital bed. A bumper tail can be positioned around at least a portion of the bed. The bumper rail bulges farther from the bed at bed corners than from other bed locations. The system can further comprise a support bar engaged to the elevating member which is constructed and arranged to lift the bar. A biasing mechanism can exert a force on the horizontally sliding bar reducing the separation distance between the at least one engagement member and the vertically extending support bar. The horizontally sliding bar can have an inner portion in a telescoping relationship to the outer portion. The horizontally sliding bar can be pivotably engaged to the at least one engagement member.

This and other aspects of the invention are described in more detail in the accompanying description and drawings.

BRIEF DESCRIPTION OF THE SEVERAL VIEWS OF THE DRAWINGS

The invention is best understood from the following detailed description when read in connection with accompanying drawings, in which.

DETAILED DESCRIPTION

A common form of patient transport device comprises a patient holding apparatus used together with a mobile IV pole. Mobile IV pole design is constrained by two contradictory physical requirements. Mobile IV poles must simultaneously have a base sufficiently wide so that the poles are stable and do not easily fall over, and which are sufficiently narrow so that the IV pole may be positioned adjacent to a patient holding apparatus such as a wheelchair, wheeled bed, stretcher, gurney, or the like. Lack of attention to either of these two design requirements may be problematic tendering the IV pole in-operable. An IV pole with a narrow base may be unstable and potentially fall over, which may either pull out an IV lead from a patient or cause other physical injury. In addition, the tipping over of an IV pole may result in the bag or pumps being positioned below the patient, resulting in poor or non-transfusion of needed fluids into the patient. Alternatively an IV pole having a base which is overly wide may prevent the IV pole from being positioned proximate to the patient holding apparatus, and being cumbersome to move along with the patient holding apparatus. One such novel patient transportation device is described in commonly owned co-pending patent application Ser. No. 11/711,478 the contents of which are hereby incorporated by reference in their entirety.

Figures 1, 1A:
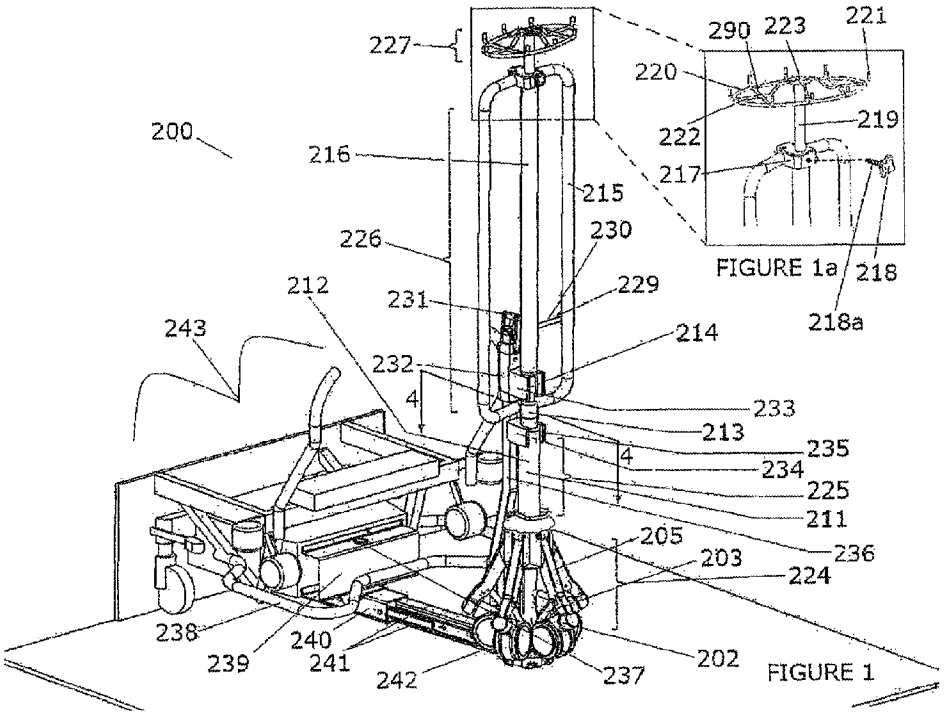
FIG. 1 is a perspective view of a self retracting IV pole in the retracted configuration supported by a bed mount.
FIG. 1a is a close up view of the top of a self retracting IV pole.
Figure 2:
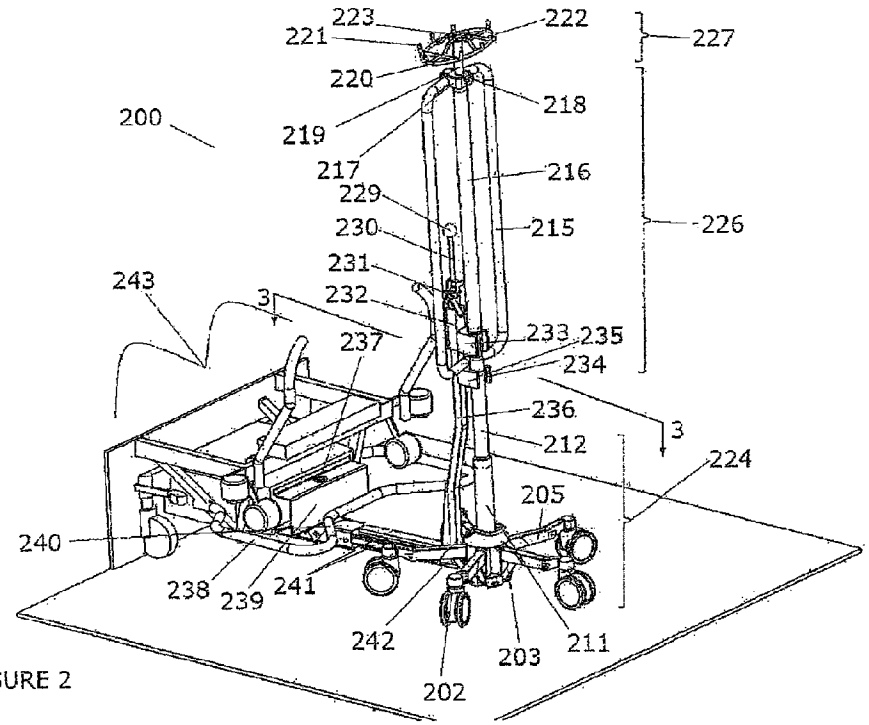
FIG. 2 is a perspective view of a self retracting IV pole in the extending configuration adjacent to a bed mount.
Figure 3:
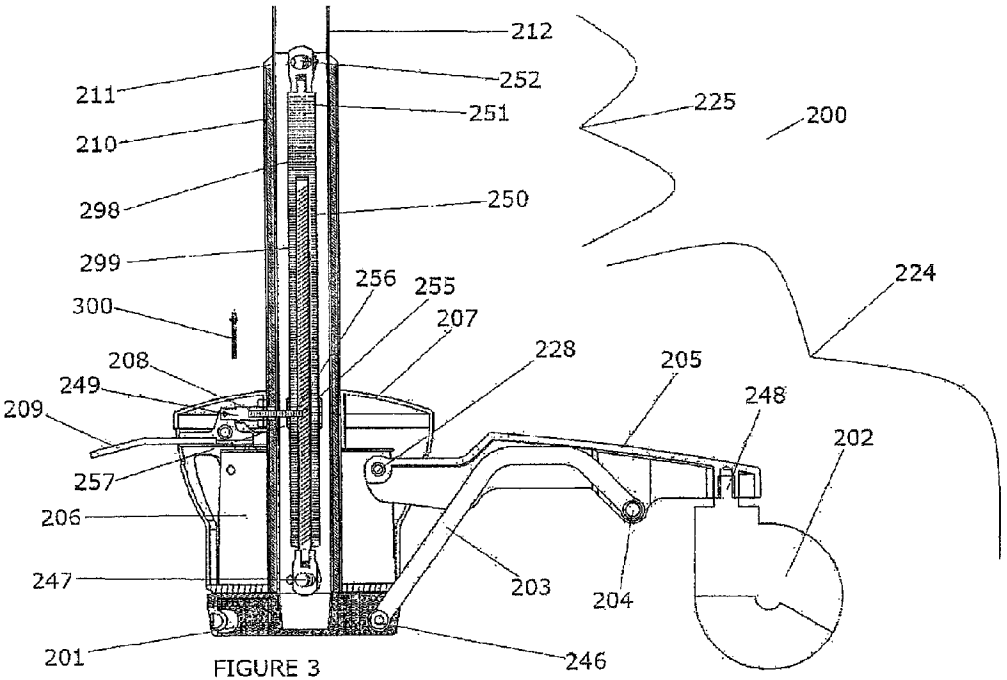
FIG. 3 is a partial detail cross sectional side view of the IV pole base taken along the line 3-3 of FIG. 2.

Referring now to FIGS. 1 and 2 there are shown an improved retractable IV pole (200) in which the legs (205) are at least in part retracted through the use of a lifting mechanism such as a gas spring (item 251 in FIG. 3). The lifting mechanism allows fox non-user powered retraction of the base (224) of the IV pole (200). In at least one embodiment, the IV pole (200) comprises a base (224) which stabilizes the IV pole (200), a top (227) where equipment can be hung, and a main mast (216) extending between the base (224) and the top (227). FIG. 1 shows the IV pole (200) in its retracted state and FIG. 2 shows the IV pole (200) in its expanded state.

In both FIG. 1 and FIG. 2 the IV pole (200) is releasably engaged to a bed mount (243) or other patient holding apparatus. Though this engagement, the IV pole (200) and apparatus can easily be moved together by one person potentially with one hand.

Attached at or near the end of each leg (205) is at least one wheel (202). In at least one embodiment, the wheels are caster type wheels capable of freely rotating along a leg-wheel connection (248). Although in this particular depiction there are five legs (205) with five four-inch caster type wheels (202), embodiments with different numbers of legs (205) (such as 1, 2, 3, 4, 5, 6, 7, 8, 9, 10 or more) and different sized or types of wheels (202) are contemplated by the inventive concept.

Figure 4:
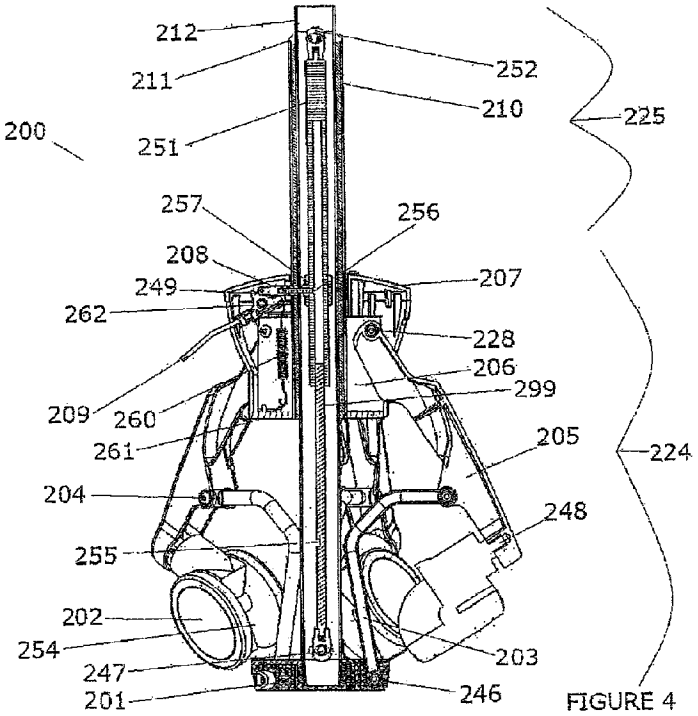
FIG. 4 is a partial detail cross sectional side view of the IV pole base taken along the line 4-4 of FIG. 1.

The base (224) of the IV pole (200) comprises two or more legs (205) which are pivotably engaged to the IV pole (200) by leg connections (228). As illustrated in FIGS. 3 and 4, the leg connections can be pins, screws, nuts or any other pivoting engagement known in the art. When in the expanded state (as in FIG. 2) the legs (205) are pivoted to extend away from the mast (212) of the IV pole (200) to provide a stable support platform. When in the retracted state (as in FIG. 1) the legs (205) are oppositely pivoted and extend closet to the mast (212) of the IV pole (200) allowing the IV pole (200) to be moved close to another object.

Referring now to FIG. 3 there is shown an embodiment of the base (224) of the IV pole (200). A gas spring (251) automatically retracts the base (224) once the gas spring (251) is actuated. Gas springs are well known in the art and are described at least in U.S. Pat. Nos. 7,222,702, 7,073,642, and 4,582,304 all of which are incorporated by reference in their entirety.

In general gas springs (which are also sometimes referred to as gas props, shocks, dampers, struts or lifts), use compressed, high-pressure fluid to assume a longer configuration, which in turn exerts a pushing force capable of extending or supporting items. Typically, the gas is located within a cylinder, and is compressed by a rod (or piston rod). The rod in turn exerts a pushing force against a plunger which is firmly positioned against the rod. The pushing force imposes friction when the gas spring is compressed or extended. Gas springs can resist or become rigid in response to tension or compression. In at least one embodiment, at least a portion of the mast (212) is hollow and the Gas Spring (251) is located within the hollow portion.

In at least one embodiment a 16-Series Gas Spring manufactured by SUSPA Inc., of Grand Rapids Mich. is used in the IV Pole (200). In at least one embodiment, the gas spring (251) facilitates retraction of the legs by elevating at least a portion of the base (224) when it transitions from its shorter configuration to its longer configuration when transitioning to its longer configuration it pushes on portions of the IV pole (200) which in turn pull the legs (205) toward the mast (212) and pull the wheels (202) up off of the ground.

In at least one embodiment, the IV pole (224) comprises a base support (206) located at or near the bottom of the mast (212). In at least one embodiment, the base support (206) is positioned around a portion of the mast (212). The base support (206) is one location where the leg (205) is pivotably engaged to the IV pole by at least one leg connection (228). As the elongating gas spring (251) pushes the base support (206) upward, the portion of the leg (205) near leg connection (228) is also moved upwards. This upward movement in turn rotates the portion of the leg-wheel connection (248) where the wheel (202) is engaged to the leg (205) into a position closer to the mast (212).

In at least one embodiment, the gas spring (251) is released into the longer configuration by moving a gas spring pin (208). The gas spring (251) is biased by fluidic pressure to elongate and is restrained in the shorter configuration by the gas spring pin (208). In at least one embodiment, the gas spring pin (208) has a length which in the shorter configuration (as shown in FIG. 3) extends through a pin aperture (255) in the gas spring plunger (299). By extending into the pin aperture (255), the gas spring pin (208) blocks the gas spring plunger (299) from extending. When the gas spring pin (208) is pulled out of the pin aperture (255) (as shown in FIG. 4), the gas spring plunger (299) is no longer restrained and the gas spring is pushed into the longer configuration by the fluidic pressure. This in turn causes the base support (206) to be moved upwards in the direction of arrow 300 in FIG. 3. The inventive concept also contemplates all other mechanisms known in the art of restraining gas springs from expanding and releasing gas springs to expand.

In at least one embodiment the gas spring pin (208) also passes through an aperture (256) in the gas spring cylinder (298) which is aligned with the pin aperture (255) in the shorter configuration. In at least one embodiment, the aperture (256) in the gas spring cylinder (298) and the gas spring pin (208) are surrounded by a fluid proof shroud (257). The shroud prevents leakage of pressurized fluid from within the gas spring cylinder (298) through the gas spring cylinder aperture (256) while allowing free movement by the gas spring pin (208). In at least one embodiment, the shroud 57 is flexible and is engaged to the gas spring pin (208) and the gas spring cylinder (298).

In at least one embodiment, the gas spring pin (208) is in mechanical communication with a gas spring pin release (209). As shown in FIG. 4, when the gas spring pin release (209) moves the gas spring pin (208) enough, the gas spring (251) is freed to expand into the longer configuration. The gas spring pin release (209) can be a pedal and can be positioned to be easily moved or depressed by a person's foot. As shown in FIG. 3, in at least one embodiment the gas spring pin release (209) is connected to a pin release joint (249) which is also engaged to the gas spring pin (208). The gas spring pin release (209) pivots in response to being depressed. The pivoting motion of the gas spring pin release (209) levers the pin release joint (249) farther away from the gas spring (251) this in turn pulls the gas spring pin (208) away from the gas spring (251) and frees the gas spring (251) to elongate.

The gas spring pin release (209) can also be engaged to the base support (206). Some or all of the base support (206) can be surrounded at least in part by a housing (207) the housing (207) can contain all of the components which may facilitate the actuation of the gas spring (251) (including but not limited to some or all of the gas spring pin release (209), the gas spring pin (208), and/or the leg connections (228). The housing (207) can also comprise a hygienic fluid tight seal to prevent the entry of liquids, blood, organic matter or other material into the interior of the IV pole base (224) which may drip or splatter against the IV pole during use.

In at least one embodiment, the IV pole (200) also comprises a base center (201) located at the bottom of the mast (212) which provides a load bearing bottom that can support the weight of the IV pole (200) in the absence of the wheels (202) or when the wheels (200) are retracted. The base center (201) has larger diameter than the mast (212) in order to provide stability for the IV pole (200). The base center (201) however has a narrower diameter than the extended legs (205) in order to permit positioning the retracted IV pole (200) closer to a holding apparatus. As shown in FIG. 3, in at least one embodiment, the base center (201) and the base support (206) have substantially the same diameter. In at least one embodiment, the base center rests upon the base support (206) in the expanded configuration. In at least one embodiment, the retracted legs (205) and/or the retracted wheels (202) have the same diameter as the base support (206).

The legs (205) can receive buttressing support from one or more braces or support legs (203) which are engaged to the IV pole (200) and which are also pivotably engaged by an outer connection (204) to the legs (205). The braces (203) and or the outer connection (204) may be located at any desired position along the legs (205), so long as the performance of the functional features described herein are not sacrificed.

In at least one embodiment, the outer connection (204) is located along the leg (205) between the leg connection (228) and the leg-wheel connection (248). In at least one embodiment the support legs (203) are pivotably engaged by a support connection (246) to the base center (201). In at least one embodiment the support connection (246) is engaged to a position at or near the bottom of the mast (212). The support connection (246) and the outer connection (204) may be pins, screws, bolts, or any other pivoting connection known in the art. When elongating into the retracted configuration, as the bottom of the mast (212) and/or the base center (201) move farther away from the leg connection (228), one or more braces (203) pull the leg (205) in a downward direction, pivoting the leg closer to the mast (212). FIG. 4 also illustrates how non-linear shaped support legs (203) are able to extend or curve around the wheels (202) in the retracted state, allowing the legs (205) to be positioned closer to the mast (212). FIG. 4 also illustrates that the brace (203) can be positioned to fit within a gap (254) in caster type wheels (202).

Although in FIG. 4 the gas spring (251) has a gas spring plunger (299) rigidly engaged to a lower portion of the IV pole by a plunger connector (247), contemplated embodiments envision the reverse orientation of the gas spring (251). In reverse orientation embodiments, the gas spring plunger (299) is positioned above the gas spring cylinder (298) and the gas spring connector (252) which connects the gas spring cylinder (298) to the mast (212) is below the plunger connector (247).

Also shown in FIG. 4 is a gas spring pin release spring (260). This spring biases the gas spring pin release (209) against being moved when in the extended configuration. The bias must be overcome by the user in order to retract the legs (205).

In at least one embodiment, the IV pole (200) comprises a base sleeve (210). The base sleeve (210) is a tube or other sleeve arrangement positioned around the mast (212) to guide the upward or downward motion of the IV pole base (224). The sleeve (210) (as well as the housing (207) prevent the entry of liquids, blood, organic matter or other material into the interior of the IV pole base (224) which may drip or splatter against the IV pole during use. A sleeve bushing (211) may be wedged between the mast (212) and the base sleeve (210) to firmly hold the base sleeve in place and seal any point of entry into the base (224). The sleeve bushing (211) may be a compressible cylindrical collar or any other shape known in the art. The sleeve bushing (211) may be plastic and may allow the base sleeve (210) to slide relative to mast (212).

In at least one embodiment, the base sleeve (210) is movable relative to the mast (212) and maintains a constant position relative to the leg connections (228), base support (206), gas spring connections (252 or 247) and/or one of the components of the IV pole base (224) or any combination thereof. In at least one embodiment at least a portion of the base sleeve (210) is at least partially surrounded by the base support (206).

Referring again to FIG. 1 it is shown that in at least one embodiment, the IV pole (200) is suspended in the air or at least supported prior to actuating the gas spring (251). By suspending or supporting the IV pole (200) prior to actuation, at least some of the weight of the IV Pole (200), is removed from the wheels (202) which facilitates a more efficient retraction of the IV pole's legs (205).

Gas springs (251) commonly undergo hysteresis, a process in which the actual force output is less than expected when initially actuated but then reaches the expected level after it has been set in motion. In at least one embodiment, an IV pole (200) which is weighed down by equipment and which due to hysteresis is otherwise too heavy to have its legs retracted by the gas spring (251) with the IV pole (200) resting on the ground, is retracted by the gas spring (251) because the legs are relieved of the added weight. In at least one embodiment, the weight is relieved by rolling the IV Pole (200) into one or more mounts (233, 234) which lift the IV pole (200) and bear the weight of the IV pole (200) and equipment.

In at least one embodiment, the IV pole (200) is adapted for engaging two mounts one being an upper mount (233) and one being a lower mount (234). In at least one embodiment the IV pole (200) is adapted by having a narrow portion (214) of the main mast (216) releasably engaged to the upper mount (233). In at least one embodiment, one or more of the mounts have a generally rounded interior with an open side facing the IV pole (200). In at least one embodiment illustrated in FIG. 7, there is shown within at least one of the two mounts is a clip (235) which is a biased gripping member (such as a strip of bent metal). The clip (235) is constructed and arranged to allow for the free passage of the IV pole (200) into the mount (233, 234) but which restrains the IV pole (200) from exiting the mount (233, 234) unless released. In particular, the lip (235) prevents the gas spring or other lifting mechanism from lifting the main mast (216) up out of the mounts (233, 234). In at least one embodiment, at least one of the mounts comprises a key port (263). The key port (263) is an aperture sized to accommodate a key slot (262 in FIG. 6) in the mast (216) to prevent twisting and sliding of the mounted IV pole. All gripping or clipping means known in the art are contemplated by the inventive concept.

Figure 6:
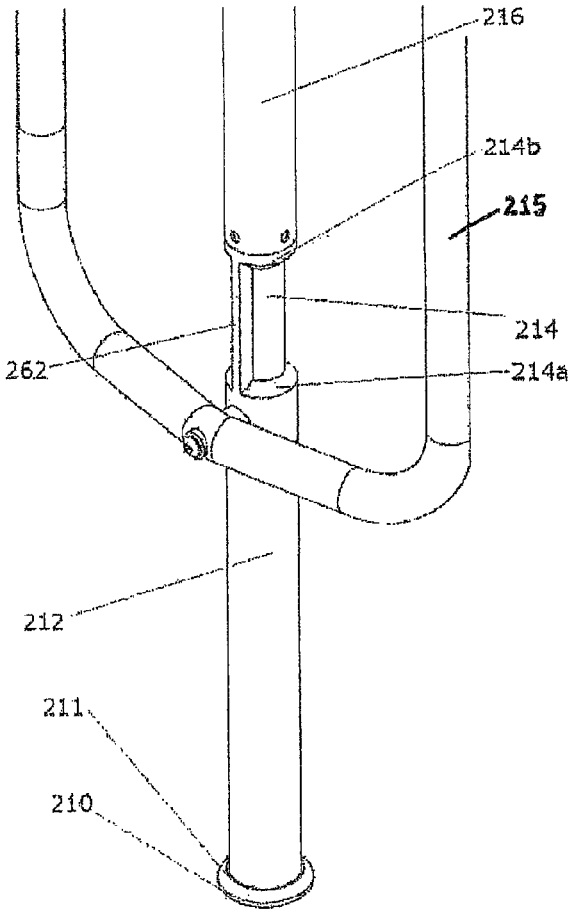
FIG. 6 is a close up perspective view of the narrow portion of the main mast.
Figure 7:
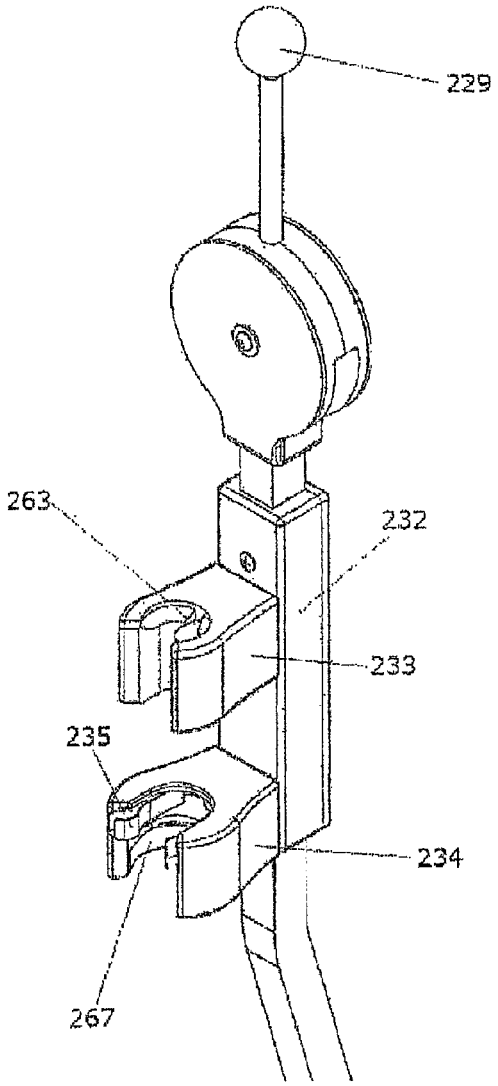
FIG. 7 is a close up perspective view of the upper and lower mounts.

Referring again to FIG. 1 it is shown that the IV pole can be wheeled towards the mounts (233, 234) and a narrow portion (214) slides within the upper mount (233). In at least one embodiment, one or more supplemental masts or wings (215) descend lower than the narrow portion (214) allowing lower placement of equipment on the wings (215) than on the main mast (216). In at least one embodiment, as illustrated in FIG. 6 there are tapering portions (214a, 214b) immediately above and below the narrow portion (214) which gradually widen to the width of the main mast (216). These tapered portions allow the IV pole (200) to be positioned above or below the mounts (233, 234) and appropriately drop or ascend into proper position. Use of tapered portions allows the user to secure the IV pole (200) to the mounts (233, 234) without needing to perfectly align the narrow portion (214) with the mounts (233, 234). In at least one embodiment there is also a key slot (262) extending from the narrow portion (214). The key slot fits within a correspondingly shaped key slot (263 in FIG. 7) and prevents any twisting or side to side movement of the IV pole (200).

Figure 8:
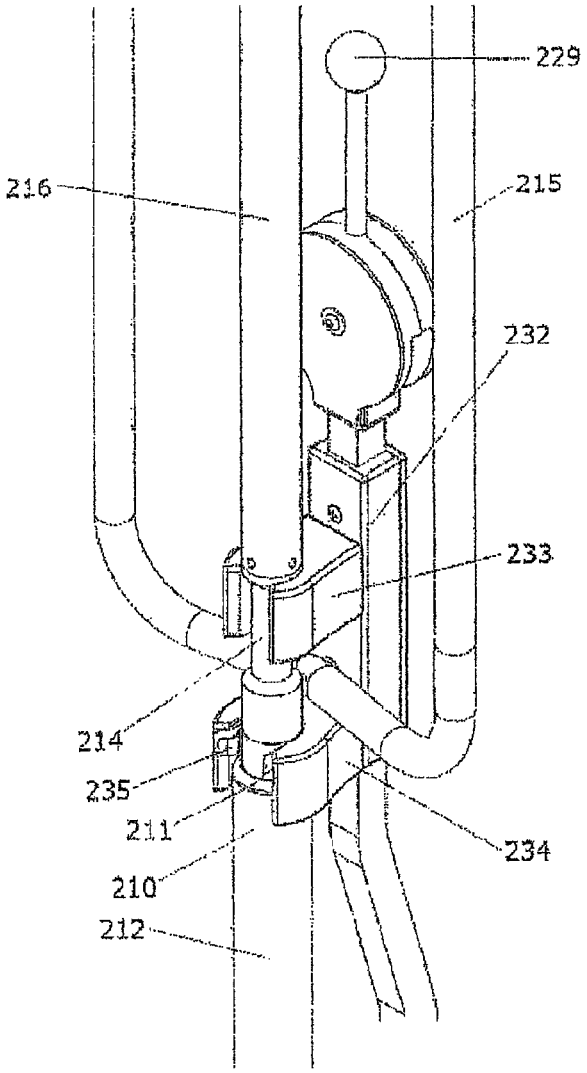
FIG. 8 is a close up perspective view of the upper and lower mounts engaged to the main mast of the IV pole.

FIG. 8 illustrates the main mast (216) supported by the mounts (233, 234). In at least one embodiment the upper mount (233) is constructed and arranged to grasp the diameter of the narrow portion (214) of the main mast (216). In at least one embodiment, the lower mount (234) is constructed and arranged to grasp the diameter of the sleeve bushing (211) or base sleeve (210). In at least one embodiment, the lower mount (234) has a clip or other portion sized to grasp the diameter of the mast (212) and a sleeve slot (267) which larger and is constructed and arranged to grasp the wider diameter of the sleeve bushing (211) or base sleeve (210).

As shown in FIGS. 1 and 2, in at least one embodiment, when the IV pole (200) is properly positioned within the mounts (233, 234), as the legs (205) retract, the base sleeve (211) slides upward and into the lower mount (234). This secures the IV pole (200) from easily moving out of the lower mount (234). By this method, the legs (205) can be securely positioned close to a patient holding apparatus with little effort by the user. In at least one embodiment, all the user needs to do is roll the IV pole (200) into a desired location relative to a patient transport apparatus and activate the gas spring pin release (209) to ready the IV pole (200) for easy transport FIG. 1 depicts the IV pole (200) in its retracted configuration and is off of the ground after it has already been mounted onto the bed mount (243). FIG. 2 shows the IV pole (200) suspended by the mounts (233, 234). In at least one embodiment, the mounts (233, 234) lift the IV pole (200) off the ground before activating the gas spring.

Figures 5, 5A, 5B:
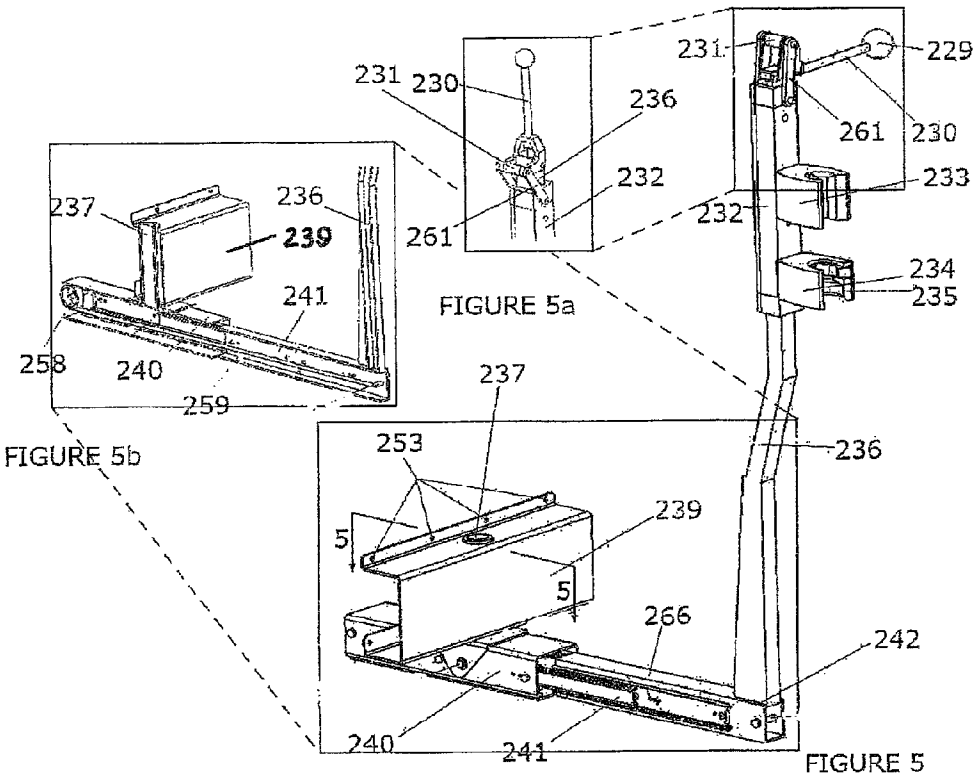
FIG. 5 is a perspective view of an extending bed mount.
FIG. 5a is a close up view of a lifting handle.
FIG. 5b is a partial detail cross sectional side view of the extending bed mount taken along the line 5-5 of FIG. 5.

Referring now to FIGS. 5, 5a, and 5b it is shown that in at least one embodiment, in which once the IV pole (200) is secured by mounts (233, 234), the operator pulls a lifting handle (229) which pulls a lifting bar (230) upon which the mounts (233, 234) are engaged. Pulling the handle (229) causes a lifting hinge (231) engaged to the handle (229) to lever upwards. Because the lifting hinge (231) is in mechanical communication with the lifting bar (230), pulling the handle (229) raises the lifting bar (230).

Illustrated in FIGS. 5 and 5a are an embodiment in which the lifting bar (232) is held aloft by a vertical mount support bar (236). The lifting bar (232) is capable of sliding up and down the vertical mount support bar (236) to alternatively raise or lower the IV pole. In at least one embodiment, the lifting bar (230) at least partially surrounds the vertical mount support bar (236) but is not directly engaged to it. Instead the lifting bar (232) is pivotably engaged to a lifting tab (261). In FIG. 5a, the lifting handle (229) is pivotably engaged to the vertical mount support bar (236) and has not been pulled. As a result, the lifting bar (232) is in a lower position along the vertical mount support bar (236). FIG. 5 however shows that as the lifting handle (229) is pulled, the lifting hinge (231) is rotated from a position on the side of the handle (229) to a higher position over the handle (229). This in turn elevates the lifting tab (261) which pulls the lifting bar (232) up the vertical mount support bar (236) to a higher position.

Lifting the IV pole off the ground reduces or eliminates any hysteresis effects and assures that the gas spring easily retracts the legs (205). FIG. 5 illustrates an embodiment in which the operator pulls of pushes the lifting handle (229) approximately 90 degrees which in turn moves the lifting hinge (231) 90 degrees and thereby lifts the IV pole just enough to get the wheels off the ground. In at least one embodiment this is approximately one inch (or less) off of the ground.

Referring again to FIG. 5 there is shown an embodiment in which the mounts (234, 233) are in movably engaged communication with a holding apparatus such as a bed. The vertical mount support bar (236) extends at least partially upwards and away from the apparatus and is in mechanical communication both with the mounts (234, 233) and the apparatus. In at least one embodiment, the vertical mount support bar (236) is engaged to a sliding mount bar (241). The sliding mount bar (241) allows for the vertical support bar (236), as well as the other component connected to the vertical support bar (236) (including the IV Pole), to move closet to the apparatus as well as farther away from the apparatus. In at least one embodiment the sliding mount bar moves horizontally with the use of a drawer glide (266). Examples of drawer glides are found in U.S. Pat. Nos. 6,626,509 and 6,485,120 the contents of which are hereby incorporated by reference in their entirety. In at least one embodiment the vertical support bar (236) can rotate via mechanical communication with a mount bar pivot (237). The rotatable communication allows for near complete 360 degree movement around the bed. This movement is important when maneuvering abed and IV pole (200) through tight areas such as, but not limited to, hallways, rooms, and elevators.

As shown in FIG. 2, in order to allow for a smooth 180 degree rotation around the bed mount (243) (which can be mounted on the head of a bed), one or more bed mount bumpers (238) can be positioned around the perimeter of at least a portion of the bed. The bumpers (238) prevent the rotating vertical support bar (236) from catching any point of the bed.

In at least one embodiment, the bumpers (238) extend along a non-rectangular path to allow closet positioning of the IV pole (200). Because the corners of the bed extends farther out relative to mount bar pivot (237) than other portions of a bed, the bumpers (238) must be farther from the mount bar pivot (237) when adjacent to the bed corners than when between the bed corners. By bulging the bumpers (238) inward at positions along the bed between the corners, the IV pole (200) can be positioned closer to the bed at those positions.

In at least one embodiment shown in FIG. 5, the sliding mount bar (241) is at least partially housed in a mount bar housing (240) which is connected to the bottom of a bed mounting bracket (239). The bed mounting bracket (239) is engaged to the actual bed and is constructed and arranged to be mountable on most. Intensive Care Unit beds as well as other patient holding apparatuses. In at least one embodiment, mount bar pivot (237) is housed within the bed mounting bracket (239) and facilitates the mount bar housing (240) to rotate up to and beyond 180 degrees.

In at least one embodiment illustrated in FIG. 5b a biasing mechanism (258) in mechanical communication with the sliding mount bar (241) exerts a pulling force which causes the IV pole (200) to tend to move close to the bed or holding apparatuses. In at least one embodiment, the biasing mechanism (258) is a retracting wheel, which is preset by a spring, coil, or the like to pull back on a retracting member (259). In at least one embodiment the retracting member (259) is a bar, coil, belt, or other item which engaged to both the biasing mechanism (258) and the sliding mount bar (241). In at least one embodiment pulling force of the biasing mechanism (258) is efficiently distributed by engaging the retracting member (259) to the sliding mount bar (241) at a position at or beneath the vertical mount support bar connection (242) where the vertical mount support bar (236) is engaged to the sliding mount bar (241).

In at least one embodiment, there is one gas spring pin release (209) on one side of the IV pole (200) and on the other side of the IV pole (200) are one or more labels indicating that the gas spring pin release (209) is not on that side. Such labels make the device more ergonomic and spare the operator time which could otherwise be wasted trying to find the gas spring pin release (209). In at least one embodiment the IV pole (200) can only fit into the mounts (233, 234) if the gas spring pin release (209) is positioned on the side of the IV pole (200) opposite the side that faces the mounts (233, 234).

In at least one embodiment the legs (205) may be outwardly extended during elevation of the IV pole (200) by the mounts (233, 234). In at least one embodiment, the legs (205) are manually pushed down by the user prior to release from the mount (233, 234). In at least one embodiment, the IV pole (200) "pops" off of the mounts (233, 234) with the application of a pushing force by the operator in a direction opposite that used to position the IV pole (200) within the mounts (233, 234). In at least one embodiment, all of the components which couple an IV pole (200) to a bed disclosed in FIGS. 1-5 are adapted for use on a wheel chair. In at least one embodiment as the legs are pushed down they contact the ground and then exert a lifting force against the mast (216). This lifting force lifts the mast (216) out of the mounts (234, 233) thereby releasing the IV pole (200).

Referring again to FIGS. 1 and 2 there are shown that in at least one embodiment, the equipment section (226) of the IV pole (200) includes one or more wings (215) and a main mast (216). The main mast (216) can be a continuation of the mast (212) engaged to the base (224) or can be a separate component engaged to the mast (212). The wings (215) may be removably attached to the equipment section (226). The equipment section (226) with or without the wings (215) may be used to hold patient equipment including but not limited to IV bags and pumps. The Wings (215) provide additional areas for attachment of patient equipment on the IV Pole (200). In at least one embodiment, at least a portion of the main mast (216) is hollow and an extending pole (219) may be at least partially housed within the hollow portion. The extending pole (219) is used to raise and support the top (227) of the IV pole (200).

As illustrated in FIGS. 1 and 1a, in at least one embodiment, at the top of the equipment section (226) is a mast collar (217). The mast collar (217) can be removably placeable at or near the top (227) of the main mast (216). The mast collar (217) may be set to allow the extending pole (219) to be adjustably raised or lowered from the equipment section (226). In at least one embodiment, a pressing member (218a) such as a bolt, screw or pin releasably applies pressure against the extending pole (219) thereby either allowing the extending pole (219) to be moved higher or lower, or to hold the extending pole (219) in place. In at least one embodiment, a knob (218) is engaged to the end of the pressing member (218a) and the holding pressure is applied or released by respectively turning the knob in one circular direction or another. In at least one embodiment, a portion of the mast collar (217) surrounds the top of the main mast (216), and a portion extends above the main mast (216). The portion of the mast collar (217) above the main mast (216) has an aperture through which the pressing member (218a) passes through to reach the extending pole (219). In at least one embodiment, the pressing member passes through apertures in both the main mast (216) and the mast collar (217). In at least one embodiment, one or more of the wings (215) are engaged to the mast collar (217). In at least one embodiment the lower portion of the wings (215) are engaged to the mast (212) by a lower wing connector (213).

The top (227) of the IV pole (200) may include a halo (220) engaged to the adjustable extending pole (219). The adjustable extending pole (219) allows for the halo (220) to be positioned at the optimal height for hanging items of medical equipment. In at least one embodiment, the halo (220) is a ring reinforced by one or more support bars (222) which radiate from an engagement point on the extending pole (219) out to the ring. In at least one embodiment the support bars (222) are reinforced by crossbars (290) that extend from one point on the ling to another and supportively intersect the support bars (222). One or more of the halo (220), halo support bars (222), and/or halo crossbars (290) can be constructed out of metal. The halo (220) can be of any shape including but not limited to circular, elliptical, ovoid, rounded, angular, curved, square, rectangular, triangular, trapezoidal, and any combination thereof.

Positioned around the halo (220) are halo hooks (221) which may also be constructed out of metal. The halo hooks (221) serve is to hold medical equipment including but not limited to patient fluid bags, IV bags, other medicine bags, and any combination thereof. The halo hooks (221) can be curved as illustrated in FIGS. 1 and 2 or can be of any other hooking shape. In addition, the halo hooks (221) can be extensions of the halo support bars (222) or can be circumferentially offset from the halo support bars (222).

In addition to using a gas spring to retract the legs, this invention contemplates embodiments in which the legs are retracted by any lifting mechanism known in the art including but not limited to hydraulic devices, electrical motors, coil springs, gears, hand cranks, magnetic repulsion devices, and any combination thereof. Contemplated embodiments envision a lowering mechanism as well which extends the legs through the lifting mechanism operating in reverse or through the use of another pushing mechanism including but not limited to gas springs, hydraulic devices, electrical motors, coil springs, gears, hand cranks, magnetic repulsion devices, and any combination thereof.

This completes the description of the preferred and alternate embodiments of the invention. The above disclosure is intended to be illustrative and not exhaustive. This description will suggest many variations and alternatives to one of ordinary skill in this art. The various elements shown in the individual figures and described above may be combined, substituted, or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claims below.

The invention claimed is:

1. An IV pole system for supporting medical equipment comprising:

a base having a plurality of legs, each of said plurality of legs comprising at least one wheel;

a mast engaged to said base said mast comprising a length, a top, and a bottom; and a lifting mechanism comprising a gas spring engaged to said base and to said mast, said lifting mechanism being constructed and arranged to position said plurality of legs in an extended configuration and in a retracted configuration, at least a portion of said wheels being disposed lower than said bottom of said mast when said plurality of legs are in the extended configuration and said wheels being radially separated from said mast in said extended configuration, said lifting mechanism being further constructed and arranged to elevate said base and to draw at least a portion of said plurality of legs inwardly proximate to said mast in said retracted configuration and to position said wheels radially proximate to said mast and to said bottom and to elevate said wheels above a surface in said retracted configuration, wherein when the plurality of legs are in the extended configuration, the wheel of each of the plurality of legs contacts the surface and the bottom of the mast does not contact the surface, and wherein when the plurality of legs are in the retracted configuration, the bottom of the mast contacts the surface.

2. The IV pole system of claim 1 said gas spring comprising:

two ends and a cylinder having a pin aperture, said gas spring further comprising a plunger, said plunger and said cylinder being movably engaged to each other, said gas spring being constructed and arranged to separate said two ends and to alter said length of said mast; and said cylinder comprising a compressible fluid, said cylinder being constructed and arranged to exert a pneumatic force on said plunger to separate said two ends, said cylinder being further constructed and arranged to exert a pneumatic force on said plunger to elevate said base and to position said at least one leg into said retracted configuration.

3. The IV pole system of claim 2 wherein said at least one leg is pivotably engaged to said mast.

4. The IV pole system of claim 3 further comprising;

a brace, said brace being pivotally engaged to said base and to said at least one leg, said pivotal engagement to said base being elevated relative to said pivotal engagement to said at least one leg when said at least one leg is in said retracted configuration.

5. The IV pole system of claim 4 wherein said cylinder is proximal to the base.

6. The IV pole system of claim 2 in which said gas spring is positioned within a hollow portion of said mast.

7. The IV pole system of claim 4 further comprising:

a gas release pin, the gas release pin being constructed and arranged to be inserted into and separated from said pin aperture, said gas release pin being constructed and arranged to actuate said gas spring.

8. The IV pole system of claim 7 further comprising:

a pedal having a pedal lever, said pedal lever being engaged to said gas release pin, said pedal lever being constructed and arranged to insert and separate said gas release pin relative to said pin aperture.

9. The IV pole system of claim 8 further comprising:

at least one wing extending substantially parallel to the mast, said at least one wing being engaged to said mast.

10. The IV pole system of claim 8 further comprising:

a halo, the halo comprising a outer frame having at least one hook projecting away from the frame, the frame being engaged to the mast proximate to said top.

11. The IV pole system of claim 8 further comprising a pole mount, the pole mount comprising a horizontally sliding bar engaged to both a vertically extending support bar and at least one engagement member, the vertically extending support bar comprising an elevating mechanism and one or more gripping members, the gripping members being constructed and arranged for engagement to the mast, the elevating mechanism being constructed and arranged to adjust a vertical position of said mast from a first position to a second position, where the second position is higher than the first position, the horizontally sliding bar being constructed and arranged to adjust a horizontal separation distance between the at least one engagement member and the vertically extending support bar.

12. The IV pole system of claim 11, the at least one engagement member being constructed and arranged to engage a hospital bed.

13. The IV pole system of claim 11, further comprising a support bar engaged to the elevating member, the elevating member being constructed and arranged to lift said bar.

14. The IV pole system of claim 11, further comprising a biasing mechanism engaged to the horizontally sliding bar, the biasing mechanism exerting a force on the horizontally sliding bar altering a separation distance between the at least one engagement member and the vertically extending support bar.

15. The IV pole system of claim 14, the horizontally sliding bar further comprising an inner portion and an outer portion wherein the inner portion is in a telescoping relationship to the outer portion.

16. The IV pole system of claim 15, wherein the horizontally sliding bar is pivotably engaged to the at least one engagement member.

17. The IV pole system of claim 11 in which the second position is higher than the first position by no more than one inch.

18. An IV pole system for supporting medical equipment comprising:

a base having a plurality of legs each of said plurality of legs comprising at least one wheel;

a mast engaged to said base, said mast comprising a length, a top, and a bottom; and a gas spring lifting mechanism being constructed and arranged to elevate said base relative to said mast, said lifting mechanism being further constructed and arranged to position said plurality of legs in an extended configuration and in a retracted configuration, at least a portion of said wheels being disposed lower than said bottom of said mast when said legs are in the extended configuration and said wheels being radially separated from said mast in said extended configuration, said lifting mechanism being further constructed and arranged to elevate at least a portion of said legs proximate to said mast in said retracted configuration and to position said wheels radially proximate to said mast and to said bottom, and to elevate said wheels above a surface, in said retracted configuration.

* * * * *